(12) United States Patent
Lynn

(10) Patent No.: US 8,480,968 B2
(45) Date of Patent: *Jul. 9, 2013

(54) LUER VALVE DISINFECTANT SWAB-POUCH

(76) Inventor: Lawrence Allan Lynn, Columbus, OH (US)

( * ) Notice: Subject to any disclaimer, the term of this patent is extended or adjusted under 35 U.S.C. 154(b) by 162 days.

This patent is subject to a terminal disclaimer.

(21) Appl. No.: 11/801,649

(22) Filed: May 10, 2007

(65) Prior Publication Data

US 2008/0038167 A1 Feb. 14, 2008

Related U.S. Application Data

(63) Continuation-in-part of application No. 11/724,812, filed on Mar. 16, 2007, now abandoned, and a continuation-in-part of application No. 11/724,888, filed on Mar. 16, 2007, now Pat. No. 7,794,675.

(60) Provisional application No. 60/836,637, filed on Aug. 9, 2006, provisional application No. 60/900,536, filed on Feb. 8, 2007.

(51) Int. Cl.
*A61L 2/00* (2006.01)
*A61L 9/00* (2006.01)
*A61L 2/18* (2006.01)

(52) U.S. Cl.
USPC ............. 422/294; 422/292; 422/28; 604/263

(58) Field of Classification Search
USPC ........... 15/104.94; 422/292, 294, 28; 604/263
See application file for complete search history.

(56) References Cited

U.S. PATENT DOCUMENTS

| 2,961,682 A | 11/1960 | Wurmbock et al. |
| 2,999,260 A * | 9/1961 | King .......................... 15/104.94 |
| 3,039,938 A | 6/1962 | Charm |

(Continued)

FOREIGN PATENT DOCUMENTS

| CA | 2 547 485 | 11/2006 |
| DE | 25 54 589 | 6/1976 |
| DE | 25 54 588 | 2/1977 |
| GB | 1596620 | * 8/1981 |

OTHER PUBLICATIONS

U.S. Appl. No. 60/796,946, filed May 3, 2006.*

(Continued)

*Primary Examiner* — Regina M Yoo
(74) *Attorney, Agent, or Firm* — Banner & Witcoff, Ltd.

(57) ABSTRACT

A disinfectant swab is disclosed which comprises a pouch sized for protecting a luer valve. The pouch preferably has shape memory for grasping the luer valve after the pouch as been advanced over the luer valve. The pouch includes a disinfectant along at least one of a inner surface and an outer surface. In one example, the shape memory can be providing by at least one elastic portion. In one embodiment the pouch has at least one disinfectant along the outer surfaces so that the outer surface of the swab can be used to prep skin, drug vials and the like. The pouch can be sized to elastically grasp on a plurality of types of luer valves and/or to elastically grasp on a tube having the approximate outer diameter of a luer lock connector or another portion of a luer lock connector. The pouch can be comprised of elastic foam and/or can have a flattened configuration when stored and/or can be stored in a flat tear able sealed package.

46 Claims, 5 Drawing Sheets

U.S. PATENT DOCUMENTS

| | | | | |
|---|---|---|---|---|
| 3,103,029 | A * | 9/1963 | Valles | 15/104.94 |
| 3,183,543 | A * | 5/1965 | Worcester | 15/104.94 |
| 3,240,326 | A * | 3/1966 | Miller | 206/361 |
| 3,450,129 | A * | 6/1969 | Brewer et al. | 600/572 |
| 3,903,345 | A * | 9/1975 | Baker et al. | 442/395 |
| 3,915,806 | A * | 10/1975 | Horlach | 435/307.1 |
| 3,945,380 | A * | 3/1976 | Dabney et al. | 604/410 |
| 4,243,035 | A | 1/1981 | Barrett | |
| 4,340,052 | A | 7/1982 | Dennehey et al. | |
| 4,440,207 | A | 4/1984 | Genatempo et al. | |
| 4,626,664 | A | 12/1986 | Grise | |
| 4,725,267 | A | 2/1988 | Vaillancourt | |
| 4,778,447 | A | 10/1988 | Velde et al. | |
| 4,826,025 | A | 5/1989 | Abiko et al. | |
| 4,959,881 | A * | 10/1990 | Murray | 15/227 |
| 5,088,146 | A * | 2/1992 | Smith et al. | 15/104.94 |
| 5,190,534 | A | 3/1993 | Kendell | |
| 5,242,425 | A | 9/1993 | White et al. | |
| D342,134 | S | 12/1993 | Mongeon | |
| 5,372,429 | A * | 12/1994 | Beaver et al. | 383/109 |
| 5,423,440 | A | 6/1995 | Castaneda et al. | |
| 5,433,705 | A | 7/1995 | Giebel et al. | |
| 5,533,708 | A * | 7/1996 | Atkinson et al. | 251/149.1 |
| 5,554,135 | A | 9/1996 | Menyhay | |
| 5,694,978 | A | 12/1997 | Heilmann et al. | |
| 5,795,343 | A | 8/1998 | Yavitz et al. | |
| 5,820,955 | A | 10/1998 | Brander | |
| 5,964,785 | A | 10/1999 | Desecki et al. | |
| 6,045,539 | A | 4/2000 | Menyhay | |
| 6,423,550 | B1 | 7/2002 | Jenkins et al. | |
| 6,602,244 | B2 * | 8/2003 | Kavanagh et al. | 604/544 |
| 6,677,258 | B2 | 1/2004 | Carroll et al. | |
| 6,753,306 | B2 * | 6/2004 | Simpson | 510/439 |
| 6,893,428 | B2 | 5/2005 | Willemstyn | |
| 6,911,025 | B2 | 6/2005 | Miyahara | |
| 7,127,771 | B2 | 10/2006 | McDevitt et al. | |
| 7,198,611 | B2 | 4/2007 | Connell et al. | |
| 7,214,214 | B2 | 5/2007 | Sudo et al. | |
| 7,316,669 | B2 | 1/2008 | Ranalletta | |
| 7,682,561 | B2 | 3/2010 | Davis et al. | |
| 7,922,701 | B2 | 4/2011 | Buchman | |
| 2002/0197738 | A1 | 12/2002 | Matsumoto et al. | |
| 2005/0115856 | A1 * | 6/2005 | Halkyard | 206/494 |
| 2005/0124709 | A1 * | 6/2005 | Krueger et al. | 521/50 |
| 2005/0124970 | A1 | 6/2005 | Kunin et al. | |
| 2006/0030827 | A1 | 2/2006 | Raulerson et al. | |
| 2007/0093762 | A1 * | 4/2007 | Utterberg et al. | 604/256 |
| 2007/0112333 | A1 | 5/2007 | Hoang et al. | |
| 2007/0185383 | A1 * | 8/2007 | Mulhern et al. | 600/121 |
| 2008/0011310 | A1 * | 1/2008 | Anderson et al. | 128/885 |
| 2008/0039803 | A1 | 2/2008 | Lynn | |
| 2008/0086091 | A1 | 4/2008 | Anderson et al. | |
| 2008/0177250 | A1 | 7/2008 | Howlett et al. | |
| 2009/0008393 | A1 | 1/2009 | Howlett et al. | |
| 2009/0028750 | A1 | 1/2009 | Ryan | |
| 2009/0041619 | A1 | 2/2009 | Cady et al. | |
| 2009/0062766 | A1 | 3/2009 | Howlett et al. | |

OTHER PUBLICATIONS

Non-Final Office Action mailed Apr. 28, 2011 in U.S. Appl. No. 11/805,381.

Final Office Action mailed Feb. 13, 2012 in U.S. Appl. No. 11/805,381.

M. Donlan,et al Protocol for Detection of Biofilms on Needleless Connectors . . . Hospital Infections Program, Centers for Disease Control and Prevention, Atlanta, Georgia 30333, 1 and Fred Hutchinson Cancer Research Center, Jour. Clinical Microbiology, Feb. 2001 vol. 39 #2 p. 750-753.

Salgado,CD et al. Increased rate of catheter-related bloodstream infection associated with use of a needleless mechanical valve device at a long-term acute care hospital. Infect Control Hosp Epidemiol. Jun. 2007;28(6):684-8.

Rupp, ME et al.Outbreak of bloodstream infection temporally associated with the use of an intravascular needleless valve. Clin Infect Dis. Jun. 1, 2007; 44(11):1408-14.

Field, K, et al.Incidence of catheter-related bloodstream infection among patients with a needleless, mechanical valve-based intravenous connector in an Australian hematology-oncology unit. Infect Control Hosp Epidemiol. May 2007;28(5):610-3.

Maragakis, Lisa L. et al.Increased Catheter-Related Bloodstream Infection Rates After the Introduction of a New Mechanical Valve Intravenous Access Port The Johns Hopkins University School of Medicine, Baltimore, Maryland Infect Control Hosp Epidemiol;27:67-70; Jan. 2006.

Abe, Chris,Zero Tolerance, Curbing Catheter-Related Blood Stream Infections Patient Safety & Quality Healthcare, Nov./Dec. 2007.

International Search Report and Written Opinion of the International Searching Authority mailed Oct. 1, 2008 in PCT/US08/06039.

Photographs of a prior art plastic flip cap for covering a septum of an arterial line, 2009.

Photographs of a prior art thin flexible plastic finger nail cover, 2009.

Menyhay, Steve et al.; "Disinfection of Needleless Catheter Connectors and Access Ports with Alcohol May Not Prevent Microbial Entry: The Promise of a Novel Antiseptic-Barrier Cap"; Infection Control and Hospital Epidemiology; Jan. 2006; vol. 27; No. 1; pp. 23-27.

* cited by examiner

LUER VALVE DISINFECTANT SWAB-POUCH

This application claims priority of Provisional Application 60/836,637, filed Aug. 9, 2006, and Provisional Application 60/900,536, filed Feb. 8, 2007, this application is a continuation in part of application Ser. No. 11/724,812 now abandoned and application Ser. No. 11/724,888 both filed on Mar. 16, 2007, now Pat. No. 7,794,675 the contents of each of these applications are incorporated by reference as if completely disclosed herein.

BACKGROUND AND SUMMARY OF THE INVENTION

As shown in the exemplary open piston valve of FIG. 2, the open piston luer valves in wide use today commonly have exposed piston faces which are engaged by the large open (but sterile) fluid channel (lumen) at the tip of the male luer during access. For any patient managed with an open piston valve, there is a clear and present danger that the piston face of the valve will be contaminated by the drug resistant bacteria, which are ubiquitous in many hospital wards. There is also a clear and present danger that these bacteria will be injected directly into the patient. In fact, anytime a male luer is pressed against a contaminated piston face, the male luer actually captures bacteria for injection into the patient. In view of this risk, it is most extraordinary that hospitals depend on the unpredictable behavior of active cleansing of the piston face to protect the patients from the direct injection of potentially deadly bacteria. It is even more extraordinary that hospitals depend on this unpredictable behavior even in the management of patients with prosthetic heart valves, bone marrow transplants, or even with profoundly low white blood cell counts.

Unfortunately, failure to disinfect prior to access poses a much greater risk of direct bacterial injection with luer piston valves than with the older small needle and septum systems they replaced. Since the distal exposed circular area of the lumen of a male luer is vastly greater than that of a 22 gauge beveled needle, capture of bacteria within the lumen of the male luer from a contaminated piston face is vastly greater than that within the lumen of the needle from the face of a penetrable septum. This difference was not fully appreciated when the open piston valves were introduced. Indeed, when the open piston valves were first introduced, physicians and nurses, perceiving the open piston valves as safe for patients as needled systems, began to freely allow the face of piston valves to be completely exposed between accesses to sources of bacterial contamination. No cap was generally applied to protect the face so the face was allowed to contaminate freely. At that time, nurses and physicians did not understand that, bacteria contaminating the faces of these valves, if not removed, are much more readily captured under the large diameter luer tip. Nor did they realize that this capture would place these bacteria within the lumen at the tip of the male luer, when the piston face is engaged by the advancing male luer. Worse, they did not know that, after such capture, these bacteria are directly injected into the patients.

A recent study confirmed the danger of direct large bolus bacterial injection associated with the open piston valves. This study evaluated the potential transmission of bacteria (such as those trapped under the luer tip) into patients when the piston face is not cleansed. In this study, control open piston valves were contaminated and then accessed by male luers without prior cleansing of the piston face. The study found that "all 15 control open piston valves (100%) showed massive transmission of microorganisms across the piston (4,500-10,000 colony-forming units)." See, Maki, et. al. Infect Control Hosp Epidemiol. 2006 January; 27(1):23-7. This potentially fatal event comprises a "bolus bacterial injection" which can occur when the faces of luer piston valves are left unprotected between accesses and the nurse then simply forgets, or is too hurried to swab the face before male luer insertion. As noted previously, in retrospect, this is not surprising since, the open distal lumen of the male luer is quite large and therefore a large number of bacteria located on the piston face are readily trapped within the lumen of the male luer when that lumen is pressed against the piston face.

To understand how hospitals found themselves widely using access systems capable of providing a mechanism for routine direct bolus injection of bacteria directly into patient's blood vessels, it is important to first comprehend the magnitude of the healthcare worker safety initiative of the 1990s. This mandate favored the expansion of the market for luer valves. Initially, open (but capped) luer valves entered the market. These were promoted as "eliminating the needle" but the ports of valves were deeply recessed and could not be internally swabbed. For this reason they were marketed with luer valve caps to cover the port between luer entries into the ports. With these valves, luer access required first, an uncapping procedure and then, a recapping procedure. Uncapping and recapping had not been required with the prior needled systems and this uncapping and recapping (and the need to mind the cap during connection) was not popular with nurses.

The luer uncapping and recapping procedure might seem a minimal effort to provide protection from contamination however, because it is to be performed while maintaining the sterility of the open interior of the cap it is somewhat cumbersome. After a sterile luer cap has been removed it is easy to contaminate its interior and easy to drop or contaminate the cap. Nurses often found it difficult to proceed with the luer access procedure while holding the little luer valve cap between the index finger and the thumb to keep its interior from becoming contaminated (as would easily happen if the luer cap is held in a closed hand). There was no widely accepted solution for what to do with the cap during prolonged connections. Furthermore, the routine replacement of an old luer cap with a new sterile luer cap, after each piggy back infusion, resulted in a significant increase in expense and this was not always easy to implement. To make matters worse, nurses were already supposed to cap the male luer after use and this was traditionally a different type of sterile cap.

In response to the unpopularity of uncapping, recapping, and storing or replacing the cap, the open piston valves were introduced. In essence the open piston valves were promoted as allowing a return to the simpler disinfectant swab maneuver which was widely used with the older penetrable split septum and needle systems prior to the introduction of the luer valves. Certainly, at the time, nascent open piston valves seemed like an advantage for both hospitals and nurses since the elimination of the thread able cap reduced global cost and the elimination of the perceived need to uncap, recap, and store or replace the cap reduced the work required for luer access.

Unfortunately throughout the hospital environment there are many sources of contamination of the piston face of luer valves and male luers if the face of the valve and tip of the male luer are not covered between connections. A piston face left exposed will become contaminated. For example, routine contact of the exposed piston face with the skin of the patient or healthcare worker, droplet nuclei from talking, coughing or sneezing, (generated by the patient, visitors, other patients, or the healthcare workers), excretions from nasal drainage, wounds, or nasal gastric tubing (carried inadvertently by hands of the patient or others or by direct contact) all comprises sources of piston face contamination with deadly, drug resistant bacteria. As noted, the pressing of a male luer against a contaminated piston face without prior cleansing will simply capture these deadly organisms within the lumen of the male and, as the above study demonstrated, like discharging a loaded gun to the patient, these bacteria will be injected in a bolus directly into the patient's vascular system as soon as fluid is injected through the male luer. In some patients the simple act of injecting these bacteria will result in irreversible contamination of a prosthesis, debilitating sepsis, and/or death.

Microorganisms are becoming more resistant to antibiotics and factors which greatly amplify the risk to the patient posed by the injection of resistant bacteria into patients due to failure to swab a piston face are increasing. As noted, factors which make patients more vulnerable to bacterial injection are a low white blood cell count, the presence of prosthetic heart valves or joints, and malnutrition, to name a few. Regardless of the vulnerability of the patient, if the bacterial injection causes clinical bacteremia, the death rate of even young and healthy children and adults is relatively high.

Patients are living longer with more prosthetic components, transplants, and vulnerabilities (as for example under the effects of chemotherapy) and therefore the risk posed by failure to swab the piston face will likely continue to increase over the next few decades unless technology such as that provided according to the present invention is broadly implemented. It is one of the purposes of the present invention to provide a simple, inexpensive luer valve disinfectant swab, which also can be employed to protect the luer valve face from contamination between uses.

In addition it is not only the valve which can be readily contaminated. The male luer end of piggy back systems are also exposed after withdrawal from the luer valve and therefore these male luers should be covered between uses (which can often be 24 hours). U.S. Pat. No. 7,040,598 assigned to Cardinal Health discusses the problems with male luer contamination and discloses an elastomeric piston, which covers the male luer, as a solution. The face of the rebound able protective piston which protects the male luer would, like the face for the piston of the luer valve, have to be swabbed with disinfectant prior to each use, which, as has been discussed, is unreliable. Therefore with the disclosed system (as for example shown in FIG. 18b) of U.S. Pat. No. 7,040,598 would have the same limitations relating to "failure to swab" but doubled because now both the luer valve and the male luer cover would need to be swabbed. Replacement of the passive protection from contamination of the male luer provided by the male luer cap with active disinfection provided by disinfectant swabbing of the face of a piston over the male luer is asking the nurse to in essence "always remember to unload both guns" (disinfect two surfaces) prior to each access. The simple act of "failure to remember" now leaves two potentially lethal sources of bacteria for direct injection into the patient's blood vessel.

The present traditional approach of capriciously allowing free exposure of the piston face to contamination with deadly pathogens, with reliance on the diligence of the busy healthcare worker to remove the deadly organisms before use, is fundamentally flawed and cannot stand the test of time. Nurses are busier, patients are becoming more vulnerable as a function of transplantation, prosthetics, and/or chemotherapy, and organism more resistant. Each year the need to reduce the dependence of patient safety on the actions and diligence of the healthcare workers increases.

It is important to understand that there are several factors which may mitigate diligence with respect to swabbing of the luer valve immediately antecedent access. First, the skin interface has long been considered the primary source of catheter contamination so that many nurses do not believe that bacteria are likely to enter through the luer valve, many lack understanding relevant the complexity of bacterial contamination and incubation. The present inventor, upon noting a nurse in the ICU fail to swab a luer piston valve prior to connection reminded the nurse that the site must be swabbed first; the response of the nurse was to simply say that this site was a valve and that "valves did not need to be swabbed". Even if the nurse knows the valve should be swabbed many do not think it to be of major importance, they may rationalize that after all, a few bacteria enter the bloodstream when one brushes the teeth. What they do not realize is that the bacteria on the faces of luer valve in hospitals are often potentially very deadly pathogens like Methcillin or Vancomycin resistant Staphylococci.

When substantial morbid and mortal risk in association with a high number of routine procedures is defined as a primary function of the diligence of a heterogeneous population of employees, a substantial degree of unnecessary injury to patients will inevitably result For this reason, hospital patient safety is no longer considered a matter reasonably subject to procedural personal preference and personal diligence. Rather, patient safety should be controlled hospital wide with reliable passive technology. Present systems are designed such that the risks to patients and to hospitals are a substantial function of diligence of the employee performing the accesses. Since this diligence is largely uncontrollable, the risks associated with open piston luer valves are largely uncontrollable. The present inventor contends that it is unacceptable for hospitals to perform hundreds of thousands of accesses to patient's vascular system without controlling all of the reasonably controllable risks associated with the access procedure.

The present invention serves to overcome the aforementioned problems of the prior art by providing a single inexpensive medical universal disinfectant swab and luer valve cover called for example the SWAB POUCH™ or SWAB POCKET™. In one embodiment the devices serves as a luer valve swab and cover. In another embodiment the device comprises a universal disinfectant skin and medical vial prep swab, a luer valve cover, and a luer lock cover. The universal device is configured to provide a wider range of multiple different functions thereby allowing the nurse to perform all of the basic functions of a swab including swabbing skin as well as all covering a plurality of luer valve types with one unified device which protects the luer valve between uses so that contamination by general exposure is prevented. Both devices are intended to be routinely carried by nurses in their lab coats and the more broadly functional universal device is intended as the only routine swab and valve cover which nurses need to carry. The device with extended functionality is capable of functioning as an essentially universally applicable disinfectant swab for skin, vials or access systems, a luer valve swab and cover (including for example a catheter terminal swab and cover, a Y site swab and cover, an extension set terminal swab and cover to name a few).

In one embodiment the invention comprises an expandable disinfectant swab member called, for example a "SWAB POCKET™" or LUER SWAB POCKET™". In a preferred embodiment the disinfectant swab member is shaped to form a collapsed or flattened pocket, pouch, or tube and is sized to, when in an un-flattened state, snuggly and/or elastically fit over a luer valve.

One embodiment comprises a disinfectant swab for protecting a luer valve wherein the swab comprises a pouch having an inner and outer surface the pouch further having shape memory and a disinfectant along at least one of the inner surface and the outer surfaces. In one example the shape memory can be provide by at least one portion of the pouch comprised of elastic material. The pouch can have at least one disinfectant along the outer surfaces so that the outer surface of the swab can be used to prep skin. The pouch can be sized to elastically grasp on at least one type of luer valve and in one embodiment to elastically grasp on a plurality of types of luer valves and/or to elastically grasp on a tube having the approximate outer diameter of a luer lock connector or another portion of a luer lock connector. The pouch can have a flattened configuration when stored and/or can be stored in a flat tear-able sealed package. The pouch can be comprised of elastic foam. The pouch can define an end for receiving the valve and a passageway within the pouch, the passage-way can be enlargeable along at least one dimension by compression of at least one portion of the pouch, as for example, by compression of opposing ends of the pouch. The pouch can have a first proximal blind sealed end and/or permanently closed proximal end and a closed but open-able distal end. The open-able distal end can be opened (as elastically opened) by compression of at least one portion of the valve. The distal end can elastically rebound to grasp the luer valve when the compression is released. The pouch can have an open-able end (or another more proximal portion) of sufficient length, such that the pouch can still be dilated by compression after it has been installed on the valve. In an example a proximal portion of the pouch can have opposing edges which extend outwardly from the luer valve so that the passage way can be dilated to release the elastic grasp of the wall of the pouch upon the luer valve by the application of compression (as induced by the index finger and thumb) on the edges. The pouch can then be retracted without any (or any significant) retracting longitudinal force being transmitted to the valve or any adjacent catheter attached to the valve. The pouch can defines oppositely facing walls, the walls can define a more central wall portion and more lateral wall portion, the more lateral portion having thicker walls than the more central portion so that dead space between the walls after the pouch has been installed over the valve is reduced.

In one embodiment, the disinfectant swab member has two closed ends, a blind proximal end and an open-able distal end for receiving the luer valve. The disinfectant swab member can comprise and/or contain and/or be coated with, and/or impregnated with, a disinfectant and/or one or more anti-infective agents such as chlorhexidine, alcohol, povidone iodine, or an antibiotic, to name a few. In one embodiment the disinfectant swab member can be comprised of medical grade foam which can be elastic. The entire disinfectant swab member can be comprised of elastic foam or the foam can be provided on the inside of the pouch. The disinfectant swab member can be comprised of medical grade foam and a coating or jacket of polymer and/or fabric may be provided on the outside or inside of the pocket. The memory and/or elasticity and/or the compressibility of the swab pocket over the valve can retain the swab pocket over the luer valve. This can, for example, be polymeric or fabric related memory for the flattened state in which the device may be packaged. In one embodiment the swab pouch has been coated internally with a mixture of chlorhexidine and 70% alcohol and externally with 70% alcohol alone (or the reverse with 70% alcohol alone on the inside can be applied). In one embodiment the pouch is entirely comprised of fabric which can be elastic and/or absorbent.

As noted, the universal swab-cover may be comprised of medical grade foam in the form of a foam pouch. The foam can be shaped to elastically retain the universal swab-cover over the luer valve. For example the universal swab-cover may be comprised of a single rectangle of thick elastic foam pouch comprised of opposing and/or contacting medical foam walls of about 1.5-2 cm thickness. The distal end of the foam pouch can be closed by expansion of the elastic foam at rest.

In an embodiment, the universal swab-cover can have a thinner foam wall proximally, the uncompressed and compressed foam at the distal (luer receiving end) can elastically hold the universal swab-cover in place. In addition, the distal end of the universal swab-cover provides a more rounded target configuration for direct receipt of the luer valve without the need (or with less need) for antecedent "change purse" type opening by compression of the ends, while at the same time protecting the interior from contact contamination. The elastic foam is compressed as the universal swab cover is placed over the valve and this provides one alternative type of elastic retention means to retain the universal swab cover over the valve.

In manufacture, a universal swab-cover comprised of medical grade foam can be formed by forming or cutting 3 cm by 4 cm rectangles of medical foam with a thickness of about 1.5-2.5 cm thick medical foam and then slitting the rectangles longitudinally to form a pouch with a blind proximal end. The pouches may alternatively be formed by longitudinally folding the sheet and the sealing (as by welding) along the two sides. Alternatively the universal swab-cover may be molded or woven to form the pouch.

In a preferred embodiment, the universal swab-cover is sized to be snugly and elastically retained over conventional female luer lock housing. Since many luer valves includes a female luer lock housing distal the valve, the universal swab-cover can be sized to elastically hold onto the diameter of the female lure lock housing. According to one aspect of the present invention, the female luer lock housing provides a central universal target diameter for sizing an elastic universal swab-cover to assure retention.

As shown in U.S. Pat. No. 7,184,825 (which is incorporated by reference as if completely disclosed herein to provide background for the present invention), the diameter of the outer wall of the valve adjacent the distal end often approximates the diameter of a female threaded luer lock connector and according to the present invention this diameter can comprise one target diameter for the universal swab-cover in the expanded (open mouth) position. The universal swab-cover can be comprised of elastic material which is flattened at the open end and opened (like an elastic change purse) by compression of the finger and thumb perpendicular to the long axis of the closure. This configuration and mechanism of opening provides a high degree of flexibility for elastic retention on luer valves of various diameters since the lateral portions of the pouch (the length of which can be defined by the length of the closed end) can extend beyond the diameter of the valve and still provide retention in an elastic "fish mouth" configuration on the sidewalls of the valve. In one embodiment the material is thicker (or more reboundable) adjacent the sides than the center so that the sides which extend beyond a smaller diameter luer valve housing have a stronger rebound force for closure.

Alternatively the universal swab-cover can be packaged in a more "open pocket shape" with a distal opening being slightly closed or slightly open (with or without the interior and/or distal end filled with compressible foam). The universal swab-cover can comprise a narrower or more elastic neck with or without an enlarging distal end to provide a shape memory to providing tight engagement with the valve while allowing easy insertion over the valve. The neck or opening can be squeezed at the time of application over the valve to open it or enlarge the opening. The tight elastomeric neck with an enlarged distal end allows for a generally universal secure attachment to different shaped valves. The tight neck may also be employed to reduce the potential loss of a volatile disinfectant (if employed).

In an embodiment, a portion for attachment to the branch of a Y site such as a slit and/or Y site receiving channel and/or Y site receiving latch may be provided adjacent the open-able end. The portion for attachment to the branch of a Y site may have at least one elastic portion for receiving the branch and for elastically holding the universal swab-cover over the branch to secure the valve to and over the valve or septum terminal adjacent the branch.

In an embodiment, the universal swab-cover is comprised entirely of non elastic material. In an example the inner layer can comprise a thin layer of absorbent cotton impregnated with a chlorhexidine and/or alcohol. An outer layer can be provided comprised of polyethylene terephthalate. The universal swab-cover may be specifically formed to fit over a specific valve shape. In the alternative, or in combination, a tether, latch or other connecting member may be provided for securing the universal swab-cover to the valve.

One method for protecting a patient from the transmission of bacteria through a medical valve, the valve defining a face and a valve stem comprises at least the step of placing an elastic pouch over the face and valve stem for a sustained period when the valve is not in use this can include the step of dilating the pouch as by squeezing the pouch and/or rubbing the pouch against the face. This can be accomplished for example by pressing against the outer surface of the pouch to press disinfectant from the pouch into forceful contact with the face.

It is the purpose of the present invention to provide a system and method, which is designed to provide an inexpensive combined disinfectant swab, valve cover, which can provide this enhanced passive and active protection for a cost which does not greatly exceed the cost of the conventional prepackaged chlorhexidine and/or alcohol disinfectant swab itself.

It is the purpose of the present invention to provide a system and method, which is designed to provide an inexpensive combined disinfectant swab, valve cover, which can replace the conventional disinfection swabs in hospitals with more versatile and more universally applicable combined passive and active microbiological protection technology.

It is the purpose of the present invention to provide a flexible, collapsible combined disinfectant swab, valve cover, which has a flatted configuration when packaged so that nurses can easily carry and store large numbers of these as they do presently for conventional swabs.

It is the purpose of the present invention to provide a combined disinfectant swab, luer valve cover, which defines a blind pouch which has an open-able distal end, which has memory for the closed state and spontaneously closes in the resting position.

It is the purpose of the present invention to provide a combined disinfectant swab, luer valve cover, which does not require threading onto the valve and which does not transmit torsion and/or longitudinal force to the valve or connecting catheter when applied over the valve.

It is the purpose of the present invention to provide a combined disinfectant swab, luer valve cover, which has an open-able portion, which spontaneously holds onto the valve after the swab has been placed over the valve.

It is the purpose of the present invention to provide a combined disinfectant swab, luer valve cover, which is comprised of an elastic pouch (which can be comprised of medical grade elastic foam) containing disinfectant, which disinfectant can comprise an anti-infective gel which fills the pouch.

It is the purpose of the present invention to provide a universal combined disinfectant swab, luer valve cover, and luer lock connector cover which is comprised of an elastic foam which elastically retains the universal swab-cover over the luer lock connector as well as valves of various shapes.

It is the purpose of the present invention to provide a combined disinfectant swab, luer valve cover, which comprises a pouch and includes disinfectant on both the inner surface and outer surface of the pouch to provide a mechanism for the, "SWAB AND PROTECT™ " or the, SWAB AND COVER™ procedure with a single swab system.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DESCRIPTION OF THE PRESENTLY PREFERRED EXEMPLARY EMBODIMENTS

Figure 1:
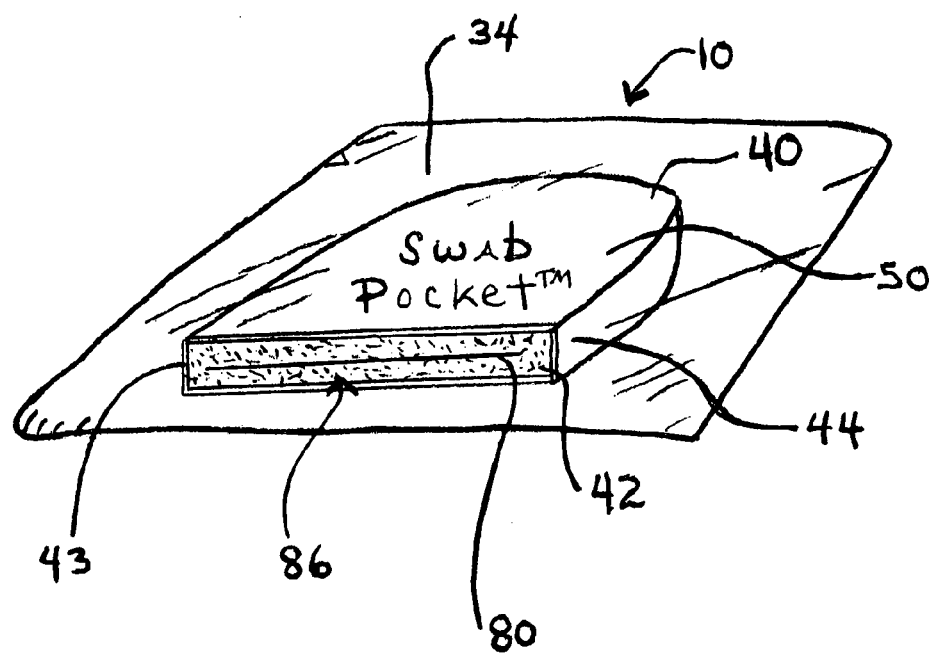
FIG. 1 is a perspective view of a universal combined disinfectant swab and valve cover called a Swab-Pocket™ or Universal Swab-Cover™ or Universal Swab & Prep-Cover™.

FIG. 1, shows an embodiment of a combined disinfectant swab, luer valve swab and cover, called a Swab Pocket™ or Universal Swab-Cover™ 10.

In a preferred embodiment the universal swab-cover 10 is shaped to form a collapsed or flattened pocket, pouch, or tube and is sized to, when in an un-flattened state, snuggly and/or elastically fit over a luer valve 11 (FIG. 2) and particularly the female luer lock housing 12 which surrounds the male luer 14. The universal swab-cover 10 can include or be comprised of at least one component with shape memory. According to one aspect of the present invention, the female luer lock housing 12 of the male luer lock connector 15 provides a relatively universal target diameter for sizing the universal swab-cover 10 to assure retention over a plurality of luer valves.

Figure 2:
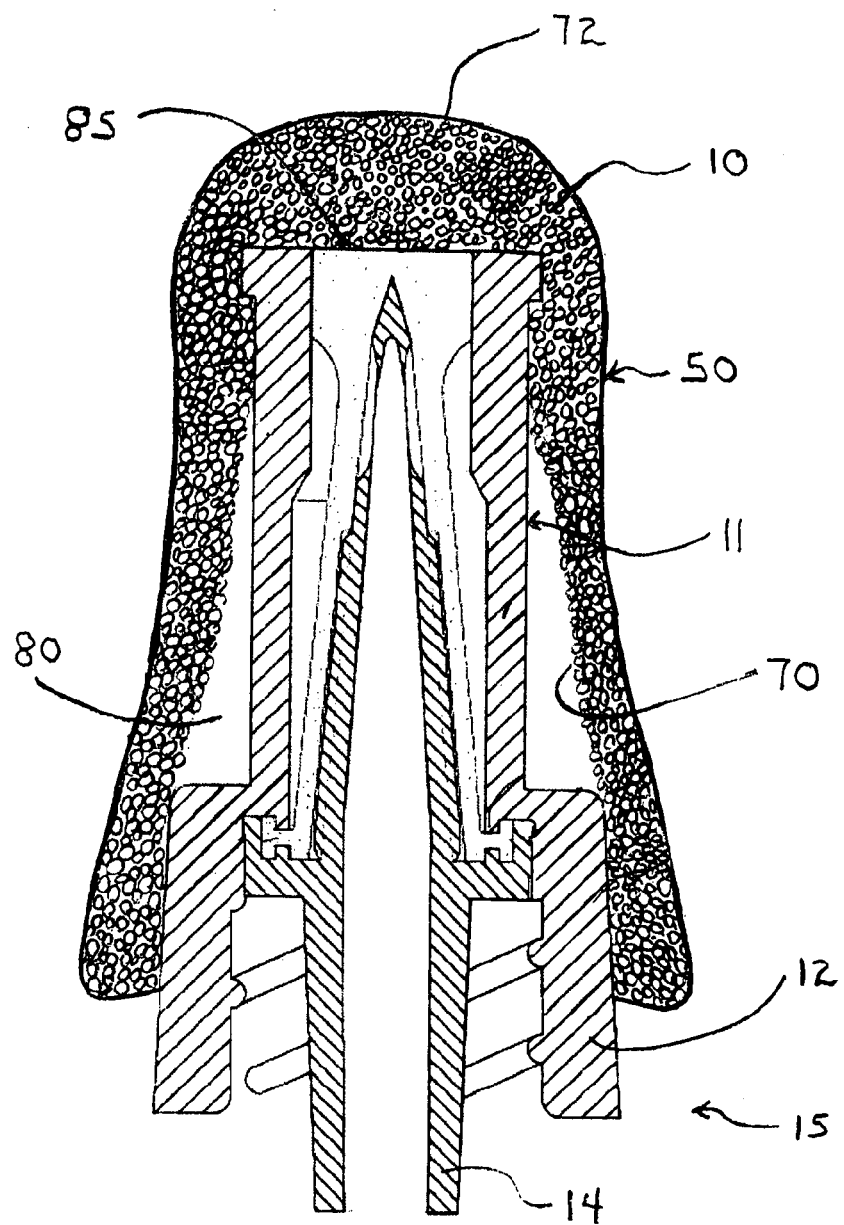
FIG. 2 is a longitudinal section view through a luer receiving valve covered by a universal swab-cover comprised of medical grade foam.
Figure 3:
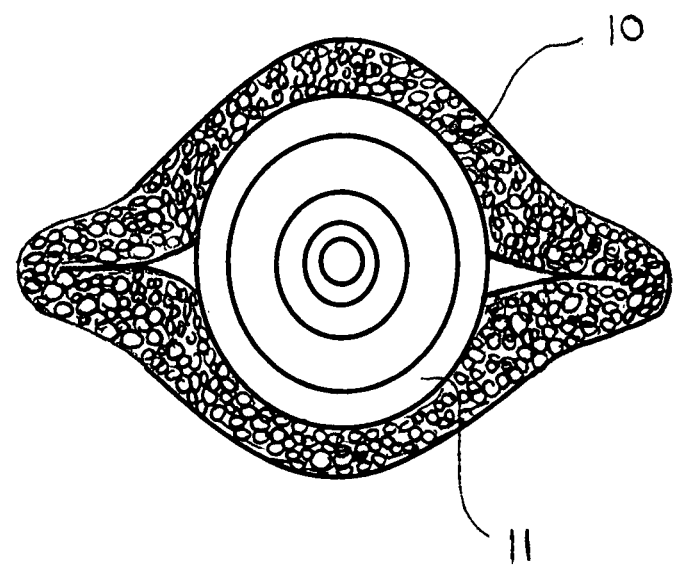
FIG. 3 is a transverse section view of the universal swab-cover through lines 3-3 of FIG. 2.

As shown in FIG. 1, one embodiment of the universal swab-cover 10 has two closed ends, a blind proximal end 40 and an open-able distal end 42 for receiving the luer valve 11 (FIG. 1) which in this figure is connected distally to a luer lock connector 15 (FIG. 2). The universal swab-cover 10 can comprise and/or contain and/or be coated with, and/or impregnated with, a disinfectant and/or one or more anti-infective agents such as chlorhexidine, alcohol, povidone iodine, or an antibiotic, to name a few. In an embodiment the swab pockets are brightly colored and/or the swab or package includes a bright trademark such as BD™ or 3M™. Since such swabs and covers will be ubiquitous in hospitals, this provides high visibility of the trademark throughout the hospital.

Figure 4:
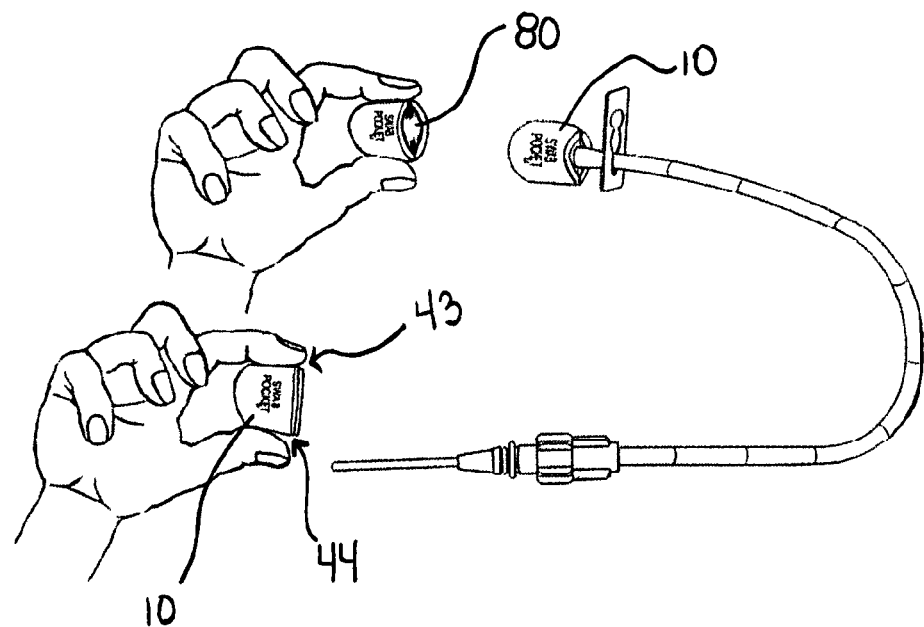
FIG. 4 is an action sequence showing one method of applying a universal swab-cover to a luer valve.
Figure 5:
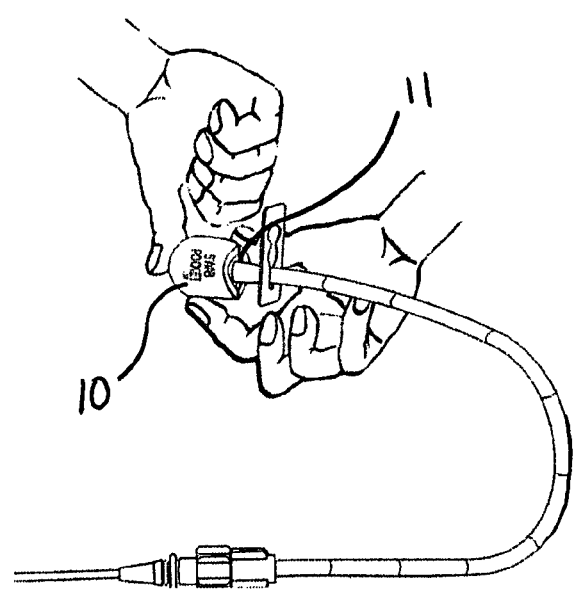
FIG. 5 is an action sequence figure showing the application of the disinfectant inner surface of a universal swab-cover to prep a luer valve before an injection.
Figure 6:
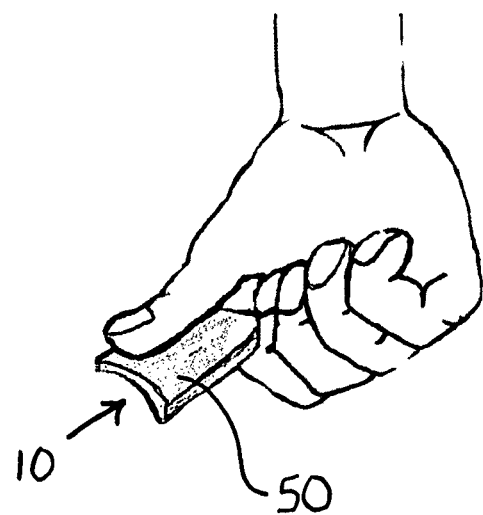
FIG. 6 is an action sequence figure showing the application of the disinfectant outer surface universal swab-cover to prep a skin before an injection.

In one embodiment the universal swab-cover 10 can be clear, opaque, florescent, and/or translucent, is packaged in a tear-able clear, opaque, florescent, and/or translucent package 34 such as that shown in FIG. 1 (similar for example to the size of the tear-able packages used for conventional alcohol prep swabs). The universal swab-covert 10 is preferably packaged with the open-able end 42 in a closed configuration as shown in FIG. 1. As shown in action sequence FIG. 4, during operation the sides 43 and 44 of the universal swab-cover 10 are squeezed, as by the index and thumb of the nurse, to open the open end 42 of the universal swab-cover 10 for subsequent non frictional or low frictional application and self retentive covering of a luer valve 11. As shown in FIG. 5, before removal the universal swab-cover 10 can be used to swab the protected luer valve 11. As illustrated in FIG. 6, when disinfectant is also provided on the outside surface 50 of the universal swab-cover 10 the universal swab-cover 10 can also be used prepping skin or prepping drug vials and the like.

In one embodiment, the universal swab-cover 10 includes an absorbent inner layer 70 preferably comprised of medical grade foam or elastic fabric with or without another absorbent material such as cotton, with an outer less absorbent or non absorbent outer layer 72, which can for example be comprised of a polymer jacket such as for example polyethylene terephthalate, polyvinyl chloride, or polyolefin to name a few. The outer layer 72 may be comprised of a very smooth elastomere which can be compressible to provide for a component of mechanical anti-infectivity and to minimize pockets of incomplete contact during wiping of the valve face as the smooth elastomere engages the smooth silicone of the valve face. The outer layer 72 can for example be an optically clear elastic silicone sleeve, coating or molded component. The outer layer 72 can for example be molded with the fabric or molded into the fabric. Alternatively the entire universal swab-cover 10 may be comprised of an optically clear elastic silicone and/or of material with elastic shape memory such as the moldable elastomere sold under the trade name Zello™ marketed by Zeller International with an internal passage way 80 containing releasable disinfectant.

In an embodiment the universal swab-cover 10 is comprised of medical grade foam with an outer coating or jacket 72 compromised of a polymer and/or fabric. In one embodiment the surface is coated with 70% alcohol and/or another disinfectant with or without an alcohol component. Alternatively, the entire universal swab-cover 10 may be comprised of medical grade foam such as for example polyolefin foam or polyvinylchloride foam, and/or other suitable medical grade material which is at least partially impermeable to reduce evaporation of disinfectant liquid (if an evaporable liquid is used) from the universal swab-cover 10. The foam can be of open or closed cell type. In the open cell type, at least a portion of the cells may contain disinfectant and the cells may be incomplete or have internal wall perforations to allow the disinfectant to escape under compression. These perforations can be very small so that escape of the disinfectant is slow and controlled or the perforations can be large so that escape is rapid upon compression of the pocket against the valve face 85, for example.

Presently most luer valves have at least one portion which has a diameter of about 1 cm. and this can provide one of the target diameters of the opened universal swab-cover 10 adjacent the distal end or mouth 86 (FIG. 1) of the universal swab-cover 10. In an embodiment, the unstretched wall thickness is about 1-5 mm and the width along the flattened axis of the distal end is about 1.5-3.0 cm so that the expanded internal diameter, when the universal swab-cover 10 is opened by compression applied by the index finger and the thumb along the distal end 86 renders a preferred target diameter range of about 7 mm-14 mm.

Although the presently preferred embodiments have been described, it will be obvious to those skilled in the art that various changes and modifications can be made without departing from the invention. While the invention has been described in connection with what is presently considered to be the most practical and preferred embodiments, it is to be understood that the invention is not to be limited to the disclosed embodiments.

The invention claimed is:

1. A medical device assembly comprising, a luer valve having a swabbable face and a pouch mounted over at least the swabbable face of the luer valve, the pouch being sized to be snuggly received and elastically retained over the luer valve for protecting the luer valve when the valve is not in use, wherein: the pouch has a proximal end and an openable distal end; the pouch is configured such that the openable distal end opens to receive the luer valve therein, by compression of at least one portion of the pouch from the outside; and the openable distal end of the pouch is elastic, the openable distal end rebounding to grasp the luer valve when the compression of the pouch is released.

2. A medical device assembly comprising, a luer valve having a swabbable face and a pouch mounted over at least the swabbable face of the luer valve, the pouch being a self-collapsible pouch sized to be snuggly received and elastically retained over the luer valve for protecting the luer valve when the valve is not in use, wherein the self-collapsible pouch defines an end for receiving the luer valve into a the self-collapsible pouch, the end of the self-collapsible pouch being enlargeable along at least one dimension by compression of at least one portion of the self-collapsible pouch from the outside, so that the luer valve can be readily received into the self-collapsible pouch, and upon cessation of said compression, said self-collapsible pouch elastically grips said luer valve.

3. The medical device assembly of claim 2 wherein the self-collapsible pouch is sized to elastically grasp on a plurality of types of luer valves.

4. The medical device assembly of claim 2 wherein the self-collapsible pouch is sized to elastically grasp on a tube having an approximate outer diameter of the threaded shroud of a luer lock connector.

5. The medical device assembly of claim 2 wherein the self-collapsible pouch has a flattened storage configuration.

6. The medical device assembly of claim 2 wherein the passageway is enlargeable along the at least one dimension by compression of opposing ends of the self-collapsible pouch.

7. The medical device assembly of claim 2 wherein the self-collapsible pouch has a first proximal blind end and a closed but openable distal end.

8. The medical device assembly of claim 2 wherein at least a portion of the self-collapsible pouch is elastic, the elastic portion elastically rebounding to grasp the luer valve when the compression of the self-collapsible pouch is released.

9. The medical device of claim 2 wherein the self-collapsible pouch has a proximal end and an openable distal end and wherein the self-collapsible pouch is configured such that an openable distal end can be opened by compression of at least one portion of the self-collapsible pouch.

10. The medical device assembly of claim 2 wherein the self-collapsible pouch has a portion of sufficient length, such that the self-collapsible pouch can still be dilated by compression after it has been installed on the luer valve.

11. The medical device assembly of claim 2 wherein the openable distal end is of sufficient length, such that the self-collapsible pouch can still be dilated by compression after it has been installed on the luer valve.

12. The medical device assembly of claim 2 wherein the self-collapsible pouch has opposing edges which project outwardly from the luer valve after the self-collapsible pouch has been installed on the luer valve so that the passageway can be dilated to release the elastic grasp of the walls of the self-collapsible pouch upon the luer valve by application of the compression induced by an index finger and thumb on the opposing edges of the self-collapsible pouch.

13. The medical device assembly of claim 2 wherein the self-collapsible pouch defines oppositely facing walls, the walls comprising a more central wall portion and a more lateral wall portion, the more lateral wall portion having thicker walls than the more central wall portion.

14. A medical device assembly for protecting a patient from the transmission of bacteria, the assembly comprising a luer receiving valve, the luer receiving valve defining a face and a valve stem, and a swab configured in the shape of a flexible self-collapsible pouch mounted over the face and valve stem and in gripping contact with the valve, wherein the self-collapsible pouch defines a distal end for receiving the luer receiving valve into the self-collapsible pouch, the distal end of the pouch being enlargeable along at least one dimension by compression of at least one portion of the self-collapsible pouch from the outside, so that the luer receiving valve can be readily received into the pouch, and upon a cessation of said compression, said self-collapsible pouch elastically grips said luer receiving valve.

15. The medical device assembly according to claim 14 wherein the swab has a flattened storage configuration.

16. The medical device assembly according to claim 14 wherein-the self-collapsible pouch defines a blind end and wherein the blind end is defined by a fold of the swab.

17. The medical device assembly according to claim 14 wherein the self-collapsible pouch defines a blind end and the blind end is defined by a seal along the swab.

18. The medical device assembly according to claim 14 wherein at least a portion of the swab is comprised of a medical grade foam.

19. The medical device assembly according to claim 14 wherein at least a portion of the swab is comprised of an elastomer.

20. The medical device assembly according to claim 14 wherein at least a portion of the swab is transparent.

21. A medical device assembly for potecting a patient from the transmission of bacteria, the assembly comprising a luer receiving valve, the luer receiving valve defining a face and a valve stem, and a swab configured in the shape of a flexible self-collapsible pouch mounted over the face and valve stem in gripping contact with the valve, wherein the self-collapsible pouch defines a distal end for receiving the luer receiving valve into a passageway within the self collapsible pouch, the passageway being enlargeable along at least one dimension by compression of at least one portion of the self-collapsible pouch from the outside, so that the luer receiving valve can be readily received into the passageway, and upon a cessation of said compression, said self-collapsible pouch elasticall grips said luer receiving valve, wherein at least a portion of the swab is comprised of a fabric.

22. A medical device assembly for protecting a patient from the transmission of bacteria, the assembly comprising a luer receiving valve, the luer receiving valve defining a face and a valve stem, and a swab configured in the shape of a flexible self-collapsible pouch mounted over the face and valve stem in gripping contact with the valve, wherein the self-collapsible pouch defines a distal end for receiving the luer receiving valve into a passageway within the self-collapsible pouch, the passageway being enlargeable alone at least one dimension by compression of at least one portion of the self-collapsible pouch from the outside, so that the luer receiving valve can be readily received into the passageway, and upon a cessation of said compression, said self-collapsible pouch elastically grips said luer receiving valve, wherein the self-collapsible pouch defines a blind end and wherein the blind end is defined by a fold of the swab, and the swab has an outer surface and the outer surface is coated with at least one disinfectant.

23. The medical device assembly according to claim 22 wherein the swab has an inner surface and the inner surface is coated with at least one different disinfectant than the outer surface.

24. The medical device assembly according to claim 22 wherein the disinfectant swab has an inner surface and the outer surface and both the inner surface and the outer surface are coated with the at least one disinfectant.

25. A medical device assembly kit comprising a luer valve and a disinfectant swab, the disinfectant swab comprising a pouch having an inner surface and an outer surface, said surfaces being provided on opposite sides of a lateral wall portion of said pouch, said pouch being sized to be snuggly received and elastically retained over said luer valve for protecting the luer valve when the valve is not in use, to thereby protect a patient from the transmission of bacteria through the luer valve, the pouch, including said lateral wall portion, comprising an elastic material elastically deformable to permit the pouch to be fitted over said luer valve and providing a gripping force to removably retain said pouch on said luer valve in contact with said inner surface, said disinfectant swab further comprising a disinfectant along at least the outer surface of said pouch, wherein at least a distal end of the pouch has an opening that is elastically enlargeable in at least one dimension by compression of at least one portion of the pouch from the outside, so that the luer valve can be readily received into a passageway thereof, the distal end being reboundable to elastically grasp the luer valve when the compression of the pouch is released.

26. A medical device assembly for protecting a patient from the transmission of bacteria, the assembly comprising a luer receiving valve, the luer receiving valve defining a face and a valve stem, and a swab configured in the shape of a flexible self-collapsible pouch mounted over the face and valve stem in gripping contact with the valve, wherein the self-collapsible pouch defines a distal end for receiving the luer receiving valve into a passageway within the self-collapsible pouch, the passageway being enlargeable along at least one dimension by compression of at least one portion of the self-collapsible pouch from the outside, so that the luer receiving valve can be readily received into the passageway, and upon a cessation of said compression, said self-collapsible pouch elastically grips said luer receiving valve, wherein the self-collapsible pouch defines a blind end and the blind end is defined by a fold of the swab, and the swab has an inner surface and the inner surface is coated with at least one disinfectant.

27. A medical device assembly comprising:
a luer valve; and
a disinfectant swab covering said luer valve, the disinfectant swab comprising a self-collapsible pouch having an inner surface and an outer surface, said self-collapsible pouch being snuggly received and elastically retained over the luer valve for protecting the luer valve when the valve is not in use, to thereby protect a patient from the transmission of bacteria through the luer valve, the self-collapsible pouch comprising an elastic material elastically deformable to permit the self-collapsible pouch to be fitted over said luer valve and providing a gripping force to removably retain said self-collapsible pouch on said luer valve in contact with said inner surface, said disinfectant swab further comprising a disinfectant along at least one of the inner surface and the outer surface of said self-collapsible pouch, wherein the self-collapsible pouch defines an end for receiving the luer valve and a passageway within the self-collapsible pouch, the passageway being enlargeable along at least one dimension by compression of at least one portion of the self-collapsible pouch from the outside, so that the luer valve can be readily received into the passageway.

28. A medical device assembly comprising a luer valve and a disinfectant swab for both swabbing and covering the luer valve, the luer valve having a swabbable face for engaging a separate male luer, the disinfectant swab being sized to be snuggly received and retained over the luer valve for protecting at least the swabbable face of the luer valve when the swabbable face of the luer valve is not engaged with said separate male luer, the disinfectant swab comprising a self-collapsible pouch having an inner and an outer surface, the self-collapsible pouch further having shape memory and a disinfectant along both the inner surface and the outer surface, wherein the self-collapsible pouch defines an end for receiving the luer valve and a passageway within the self-collapsible pouch, the passageway being enlargeable along at least one dimension by compression of at least one portion of the self-collapsible pouch from the outside, so that the luer valve can be readily received into the passageway.

29. The medical device of claim 28 wherein at least a portion of the self-collapsible pouch is comprised of an elastic material.

30. The medical device of claim 29 wherein the self-collapsible pouch is sized to elastically grasp on at least one type of luer valve.

31. The medical device of claim 29 wherein the self-collapsible pouch is sized to elastically grasp on a tube having the approximate outer diameter of a threaded shroud of a luer lock connector.

32. The medical device of claim 28 wherein the self-collapsible pouch has a flattened storage configuration.

33. The medical device of claim 28 wherein the self-collapsible pouch is stored in a flat tearable sealed package.

34. The medical device of claim 28 wherein the self-collapsible pouch is comprised of an elastic foam.

35. The medical device of claim 34 wherein the foam is comprised of open cells.

36. The medical device of claim 34 wherein the foam is comprised of closed cells.

37. The medical device of claim 28 wherein the self-collapsible pouch contains chlorohexidine.

38. The medical device of claim 28, wherein both the inner surface and the outer surface of said self-collapsible pouch comprise a medical grade foam material containing said disinfectant.

39. The medical device of claim 28, wherein in a flattened uninstalled, undeformed condition the end of said self-collapsible pouch has a width in the range of 1.5-3.0 cm.

40. The medical device of claim 39, wherein said end is openable by compression applied by finger pressure at the end to yield an opening with a width in the range of 7 mm to 14 mm.

41. A medical device assembly kit comprising:
a luer valve; and
a disinfectant swab, the disinfectant swab comprising a self-collapsible pouch having an inner surface and an outer surface, said self-collapsible pouch being sized to be snuggly received and elastically retained over said luer valve for protecting the luer valve when the valve is not in use, to thereby protect a patient from the transmission of bacteria through the luer valve, the self-collapsible pouch comprising an elastic material elastically deformable to permit the self-collapsible pouch to be fitted over said luer valve and providing a gripping force to removably retain said self-collapsible pouch on said luer valve in contact with said inner surface, said disinfectant swab further comprising a disinfectant along both the inner surface and the outer surface of said self-collapsible pouch, wherein the self-collapsible pouch defines an end for receiving the valve and a passageway within the self-collapsible pouch, the passageway being enlargeable along at least one dimension by compression of at least one portion of the self-collapsible pouch from the outside, so that the valve can be readily received into the passageway.

42. A medical device assembly kit according to claim 41, wherein said luer valve defines a face and a valve stem, and said self-collapsible pouch is a flexible pouch sized to cover the face and valve stem when said self-collapsible pouch is mounted on said luer valve.

43. A medical device assembly kit comprising:
a luer valve; and
a disinfectant swab, the disinfectant swab comprising a pouch having an inner surface and an outer surface, said pouch being sized to be snuggly received and elastically retained over said luer valve for protecting the luer valve when the valve is not in use, to thereby protect a patient from the transmission of bacteria through the luer valve, the pouch comprising an elastic material elastically deformable to permit the pouch to be fitted over said luer valve and providing a gripping force to removably retain said pouch on said luer valve in contact with said inner surface, said disinfectant swab further comprising a disinfectant along both the inner surface and the outer surface of said pouch, wherein at least a distal end of the pouch has an opening that is elastically enlargeable in at least one dimension by compression of at least one portion of the pouch from the outside so that the luer valve can be readily received into a passageway thereof, the distal end being reboundable to elastically grasp the luer valve when the compression of the pouch is released.

44. The medical device assembly kit of claim 43, wherein the pouch is dimensioned in relation to said luer valve such that the pouch can be dilated by said compression after it has been installed on the luer valve.

45. The medical device assembly kit of claim 44, wherein the distal end is sized such that the pouch can be dilated by compression after it has been installed on the valve.

46. The medical device assembly kit of claim 44, wherein the pouch has opposing edges which project outwardly from the luer valve after the pouch has been installed on the luer valve so that the passageway can be dilated to release the elastic grasp of the walls of the pouch upon the luer valve by application of the compression induced by an index finger and thumb on the opposing edges of the pouch.

* * * * *